(12) United States Patent
Albrecht et al.

(10) Patent No.: US 8,519,155 B2
(45) Date of Patent: Aug. 27, 2013

(54) CHOLINE AND TROMETHAMINE SALT OF LICOFELONE

(75) Inventors: Wolfgang Albrecht, Ulm (DE); Hans-Günter Striegel, Blaubeuren (DE); Stefan Laufer, Tubingen (DE)

(73) Assignee: c-a-i-r biosciences GmbH, Tubingen (DE)

( * ) Notice: Subject to any disclaimer, the term of this patent is extended or adjusted under 35 U.S.C. 154(b) by 0 days.

(21) Appl. No.: 13/126,216

(22) PCT Filed: Oct. 30, 2009

(86) PCT No.: PCT/EP2009/064390
§ 371 (c)(1),
(2), (4) Date: Sep. 27, 2011

(87) PCT Pub. No.: WO2010/049525
PCT Pub. Date: May 6, 2010

(65) Prior Publication Data
US 2012/0010261 A1    Jan. 12, 2012

(30) Foreign Application Priority Data
Oct. 31, 2008   (EP) ..................................... 08168127

(51) Int. Cl.
*C07D 487/06* (2006.01)
*A61K 31/403* (2006.01)

(52) U.S. Cl.
USPC .......................................... 548/453; 514/413

(58) Field of Classification Search
None
See application file for complete search history.

(56) References Cited

FOREIGN PATENT DOCUMENTS

| | | |
|---|---|---|
| EP | 0521393 A2 | 1/1993 |
| EP | 0869117 A1 | 10/1998 |
| EP | 1908757 A1 | 4/2008 |
| WO | WO 94/11332 A1 | 5/1994 |
| WO | WO 03/020267 A1 | 3/2003 |
| WO | WO 03/097041 A1 | 11/2003 |
| WO | WO 2006/083687 A1 | 8/2006 |
| WO | WO 2007/015724 A1 | 2/2007 |
| WO | WO 2007/096588 A1 | 8/2007 |
| WO | WO 2008/012110 A2 | 1/2008 |

OTHER PUBLICATIONS

Patent Cooperation Treaty International Search Report and Written Opinion for PCT/EP2009/064390, 11 pages, Dec. 11, 2009.
X. Rabasseda et al., "ML-3000. Antiinflammotory Cyclooxygenase and 5-Lipoxygenase Inhibitor", *Drugs of the Future, 20 (10)*, pp. 1007-1009, 1995.
Serajuddin et al., "Salt formation to improve drug solubility", *Advanced Drug Delivery Reviews*, vol. 59, No. 7, pp. 603-616, 2007.

*Primary Examiner* — Nyeemah A Grazier
(74) *Attorney, Agent, or Firm* — Viksnins Harris & Padys PLLP (57) ABSTRACT

The present invention relates to the choline and tromethamine salt of Licofelone.

3 Claims, 7 Drawing Sheets

CHOLINE AND TROMETHAMINE SALT OF LICOFELONE

RELATED APPLICATION(S)

This application claims the benefit of priority of European Application Serial No. 08168127.2 filed on 31 Oct. 2008.

DESCRIPTION OF THE INVENTION

The present invention relates to base addition salts of Licofelone, to a process for their preparation, a pharmaceutical preparation containing such a salt and their use.

Licofelone is the INN designation of a promising inhibitor of cylcooxygenase and 5-lipoxygenase which is suitable for the treatment of rheumatoid diseases and for the preventive treatment of allergy-induced disorders, concerning which see, for example, *Drugs of the Future* 1995, 20 (10):1007-1009. Moreover, Licofelone has chondroprotective (WO-A 03/020267), gastroprotective (WO-A 03/097041) and antineoplatic properties (WO-A 08/012,110).

None of said references describes a salt of Licofelone. It is merely mentioned that annellated pyrrole compounds represented by the general formula may form base addition salts, for instance, salts with inorganic bases, such as sodium or potassium hydroxide, or with organic bases, such as mono-, di- or triethanolamine, and the like.

The solubility of Licofelone and thus its bioavailability is rather low. Also, Licofelone undergoes degradation when stored at elevated temperatures over several weeks.

The present invention is based on the object of providing a further form of Licofelone which is improved in relation to its solubility. A further object is providing a form of Licofelone which is also improved in relation to stability.

It has now surprisingly been found that these objects are achieved by the choline and, in particular, by the tromethamine salt of Licofelone.

The present invention therefore relates to
(i) 6-(4-chlorophenyl)-2,2-dimethyl-7-phenyl-2,3-dihydro-1H-pyrrolizin-5-ylacetic acid choline salts of the formula I and (ii) 6-(4-chlorophenyl)-2,2-dimethyl-7-phenyl-2,3-dihydro-1H-pyrrolizin-5-ylacetic acid tromethamine salts of the formula II

BRIEF DESCRIPTION OF THE FIGURES

These show in

The choline salts of the invention can be characterized by their X-ray diffraction diagram (powder diffractogram). According to one embodiment, the invention relates to two crystalline forms a) and b) of a choline salt whose X-ray diffraction diagrams have the following characteristic 2θ (±0.2) values, determined with a Bruker-AXS D8 Advance powder X-ray diffractometer (Bruker-AXS, Karlsruhe, Germany), using monochromatic CuKα1 radiation and a Vantac detector (values in ° 2θ (±0.2):

a) 8.7, 12.3, 13.8, 14.2, 14.5, 15.5, 18.6, 21.5; or
b) 9.0, 9.4, 12.5, 15.4, 16.2, 17.1, 20.0, 20.3, 21.6.

Figure 1:
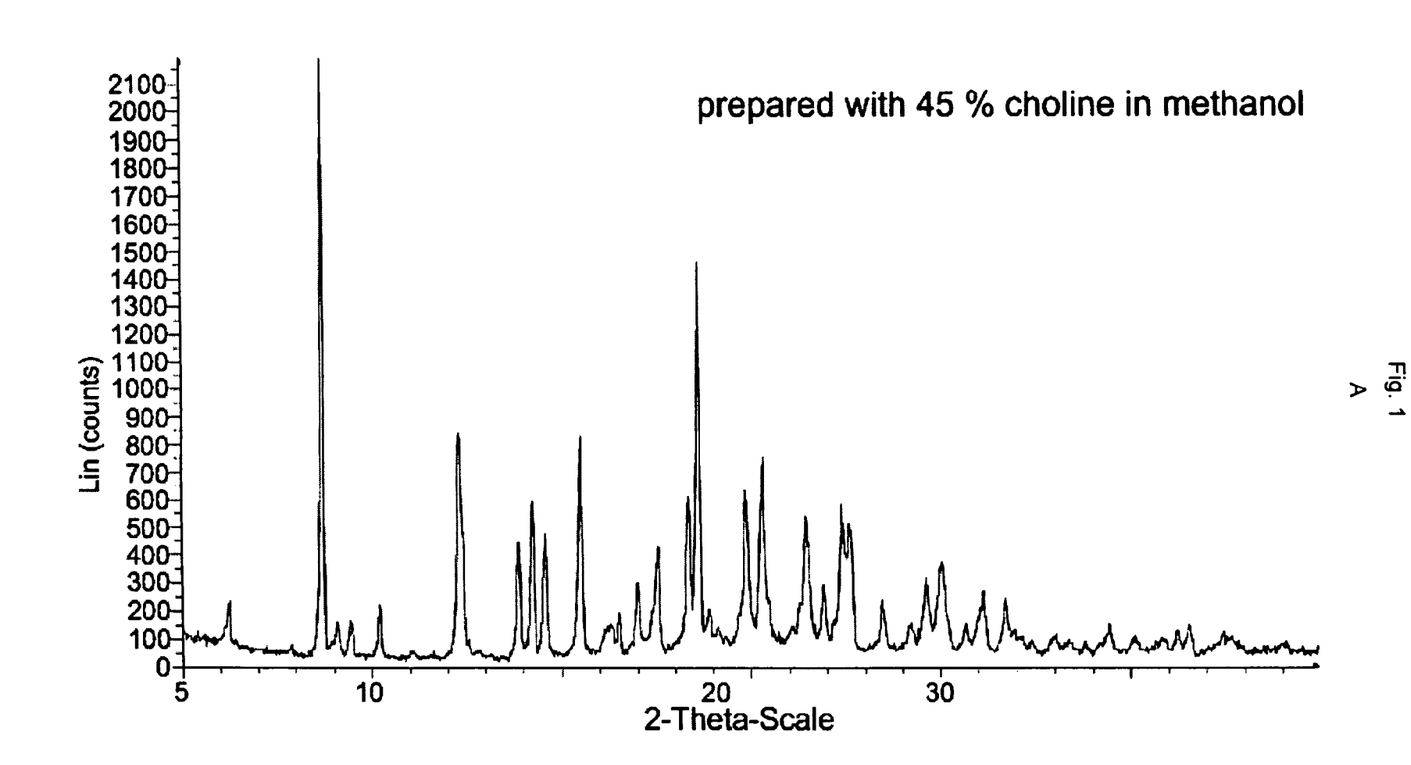
FIG. 1 the X-ray powder diffractogram of (A) the choline salt prepared in example 1A and (B) the choline salt prepared in prepared in example 1B.

According to a particular embodiment, the invention relates to a choline salt having the X-ray diffraction diagram shown in FIG. 1A or FIG. 1B.

The choline salts of the invention can also be characterized by their IR spectrum. According to one embodiment, the invention relates to a choline salt having a peak in the IR spectrum at 1580±0.5 and a peak at 1358±0.5 cm$^{-1}$. According to a particular embodiment, the invention relates to a choline salt having the IR spectrum shown in FIG. 2.

The choline salts can be produced by dissolving Licofelone in anhydrous ethanol at 50° C., adding a solution of choline in methanol to the dissolved Licofelone while heating to 65° C., evaporating a part of the solvent while allowing the mixture to cool off, adding diethylether, and recovering the precipitate.

Alternatively, the choline salts can be produced by dissolving Licofelone in anhydrous ethanol at 75° C., adding a solution of choline in water to the dissolved Licofelone while maintaining the temperature at 75° C., stirring at reflux, allowing the mixture to cool to 35° C., adding a first portion of diethylether in 15 minutes while maintaining the temperature at 35° C., adding a second portion of diethylether in 30 minutes while maintaining the temperature at 35° C., cooling the suspension in 2 h to 23° C., stirring at this temperature for about 15 h, further cooling the suspension in 2 h to −13° C., stirring at this temperature for about 2 h, and recovering the precipitate.

The tromethamine salts of the invention can be characterized by their X-ray diffraction diagram (powder diffractogram). According to one embodiment, the invention relates to a tromethamine salt whose X-ray diffraction diagram has the following characteristic 2θ (±0.2) values, determined with a Bruker-AXS D8 Advance powder X-ray diffractometer (Bruker-AXS, Karlsruhe, Germany), using monochromatic CuKα1 radiation and a Vantac detector (values in ° 2θ (±0.2): 8.5, 9.1, 9.8, 11.0, 12.8, 17.5, 17.9, 21.3, 22.0, 23.3, 24.0 and 31.6. According to a particular embodiment, the invention relates to a tromethamine salt having the X-ray diffraction diagram shown in FIG. 3.

The tromethamine salts can also be characterized by their IR spectrum. According to one embodiment, the invention relates to a tromethamine salt having a peak in the IR spectrum at 1650±0.5 and a peak at 1379±0.5 cm$^{-1}$. According to a particular embodiment, the invention relates to a tromethamine salt having the IR spectrum shown in FIG. 4.

The tromethamine salts can be produced by dissolving Licofelone in anhydrous ethanol, adding tromethamine to the dissolved Licofelone at 47° C., stirring at this temperature for about 1 h, adding diisopropylether while maintaining the temperature at 47° C., cooling the suspension in 3 h to 27° C., stirring at this temperature for about 1 h, further cooling the suspension in 1 h to −13° C., stirring at this temperature for about 2 h, and recovering the precipitate.

The choline salts of the invention show an improved solubility when compared to the free acid and also to the tromethamine salts. Licofelone choline salts are more stable than the free acid when stored at moderately elevated temperatures for several weeks.

The tromethamine salts of the invention show an improved solubility when compared to the free acid. Licofelone tromethamine salt is more stable than the free acid and the choline salt when stored at elevated temperatures for several weeks.

The Licofelone salts of the invention have proved to be a potent cyclooxygenase and/or lipoxygenase inhibitor. It is notable for a strong analgesic effect and for a similar inhibitory effect on the enzymes cyclooxygenase (CO) and lipoxygenase (LO) ($IC_{50}LO/IC_{50}CO\sim1$). They can therefore be used in the treatment of disorders associated with a change in arachidonic acid metabolism. Particular mention should be made of rheumatoid diseases and the prevention of allergy-induced disorders. The Licofelone salts of the invention thus represent an effective anti-inflammatory, analgesic, antipyretic and antiallergic agent and has antibronchoconstrictor activity and can additionally be used for the prophylaxis of thrombosis and the prophylaxis of anaphylactic and septic shock and for the treatment of dermatological disorders such as psoriasis, urticaria, acute and chronic exanthemas of allergic and nonallergic origin. In addition, they can be used for the treatment of hypercholesterolaemia.

The Licofelone salts of the invention can be administered either as single therapeutic active ingredient or as mixture with other therapeutic active ingredients. They can be administered as such, but they are generally administered in the form of a pharmaceutical composition, i.e. as a mixture of the active ingredient with one or more pharmaceutically acceptable excipients, especially carriers, diluents and/or additives. The compound or the composition can be administered, for instance, enterally, e.g. orally or rectally, or parenterally, e.g. subcutaneously, intravenously or intramuscularly, but it is preferably given in oral dosage forms.

The nature of the pharmaceutical composition and of the pharmaceutical carrier or diluent depends on the desired mode of administration. Oral compositions can be in the form for example of tablets or capsules and may comprise conventional excipients such as binders (e.g. syrup, acacia, gelatin, sorbitol, tragacanth or polyvinylpyrrolidone), fillers (e.g. lactose, sugar, maize starch, calcium phosphate, sorbitol or glycine), lubricants (e.g. magnesium stearate, talc, polyethylene glycol or silicon dioxide), disintegrants (e.g. starch) or wetting agents (e.g. sodium lauryl sulphate). Oral liquid products can be in the form of aqueous or oily suspensions, solutions, emulsions, syrups, elixirs or sprays etc. or may be in the form of dry powders for reconstitution with water or another suitable carrier. Such liquid products may comprise conventional additives, for example suspending agents, flavourings, diluents or emulsifiers. Solutions or suspensions with conventional pharmaceutical carriers can be employed for parenteral administration.

The Licofelone salts of the present invention are particularly suitable for preparing solutions of Licofelone for parental administration. For instance, the salts may be provided as a powder which is dissolved in a suitable solvent prior to administration. Suitable solvents are well known in the art and include e.g. 0.9% saline with 10% ethanol. Additionally, the solution may contain further auxiliary agents such as those commonly used for parenteral formulations, e.g. sugar alcohols and the like.

Treatment with Licofelone takes place by administering an effective amount of the Licofelone, usually formulated in accordance with pharmaceutical practice, to the individual to be treated, preferably a mammal, in particular a human. Whether such a treatment is indicated and the form in which it is to take place depends on the individual case and is subject to a medical assessment (diagnosis) which takes account of the signs, symptoms and/or dysfunctions present, and of the risks of developing particular signs, symptoms and/or dysfunctions, and further factors.

Treatment usually takes place by a single or multiple daily administration, optionally together with or alternately with other active ingredients or active ingredient-containing products, so that a daily dose of about 10 mg to about 2000 mg and in particular 10 mg to about 1000 mg is supplied to the individual to be treated.

The following examples illustrate the invention without limiting it.

X-ray powder diffractograms were recorded on a Bruker-axs D8 Advance powder X-ray diffractometer (Bruker-AXS, Karlsruhe, Germany). The sample holder was rotated in a plane parallel to its surface at 20 rpm during measurement. The measurement conditions were as follows: Radiation: Cu Kα, Source 40 kV/40 mA, divergence slit 0.6 mm, antiscattering slit 5.59 mm, detector slit 10.28 mm, start angle 2°, end angle 55°, Step 0.016° 2Θ. Raw data were evaluated using the program EVA (Bruker-AXS, Karlsruhe, Germany).

IR spectra were recorded on a Thermo Nicolet's Avatar 330 FT-IR equipped with smart endurence Diamond ATR unit for direct measurements (measurement mode: range 4000.0-500.0 cm$^{-1}$, detection limit (absolute) 0.075; sensitivity 50)

Example 1

A. Preparation of 6-(4-chlorophenyl)-2,2-dimethyl-7-phenyl-2,3-dihydro-1H-pyrrolizin-5-ylacetic acid choline salt 0.25 mol (94.97 g) Licofelone were dissolved in 1,050 ml ethanol at 50° C. 74.02 ml of a 45% solution of choline in methanol (corresponding to 0.2625 mol choline) were added and the mixture was heated to 65° C. and kept at this temperature for 30 min. Thereafter, the oil bath was removed and approx. 950 ml solvent was removed by evaporation. 500 ml diethylether were added and the white precipitate was filtered, washed with 200 ml diethylether and dried at 30° C. in vacuum.

Yield: 97.9 g (=81%), chemical purity (HPLC): 99.7% (water content: 2.2%)

An X-ray diffraction diagram of the choline salt is shown in FIG. 1A.

B. Preparation of 6-(4-chlorophenyl)-2,2-dimethyl-7-phenyl-2,3-dihydro-1H-pyrrolizin-5-ylacetic acid choline salt Licofelone (2.45 kg) was slurried in ethanol (6.6 l). The slurry was heated to 75° C. 50% aqueous choline (1.65 kg) was introduced maintaining the temperature at 75° C. and the line was rinsed with ethanol (3.2 l). The resulting solution was stirred at reflux (77° C.) for 30 min, filtered on a 0.3 μm cartridge filter and the filter was rinsed with warm ethanol (2.5 l). The solution was cooled to 35° C. and diethylether (19.3 l) was added in 15 min maintaining the temperature at 35° C. Diethylether (30.9 l) was added in 30 min keeping the temperature at 35° C. The suspension was cooled in 2 h to 23° C., stirred at this temperature for about 15 h, further cooled to −13° C. in 1 h and stirred at this temperature for 2 h. The product was centrifuged and the cake was washed with cold diethylether (7.7 l). The wet cake was dried at approx. 30° C. for 72 h.

Yield: 2.7 kg (=87%), chemical purity (HPLC): 99.84% (water content: 3.5%)

Figure 2:
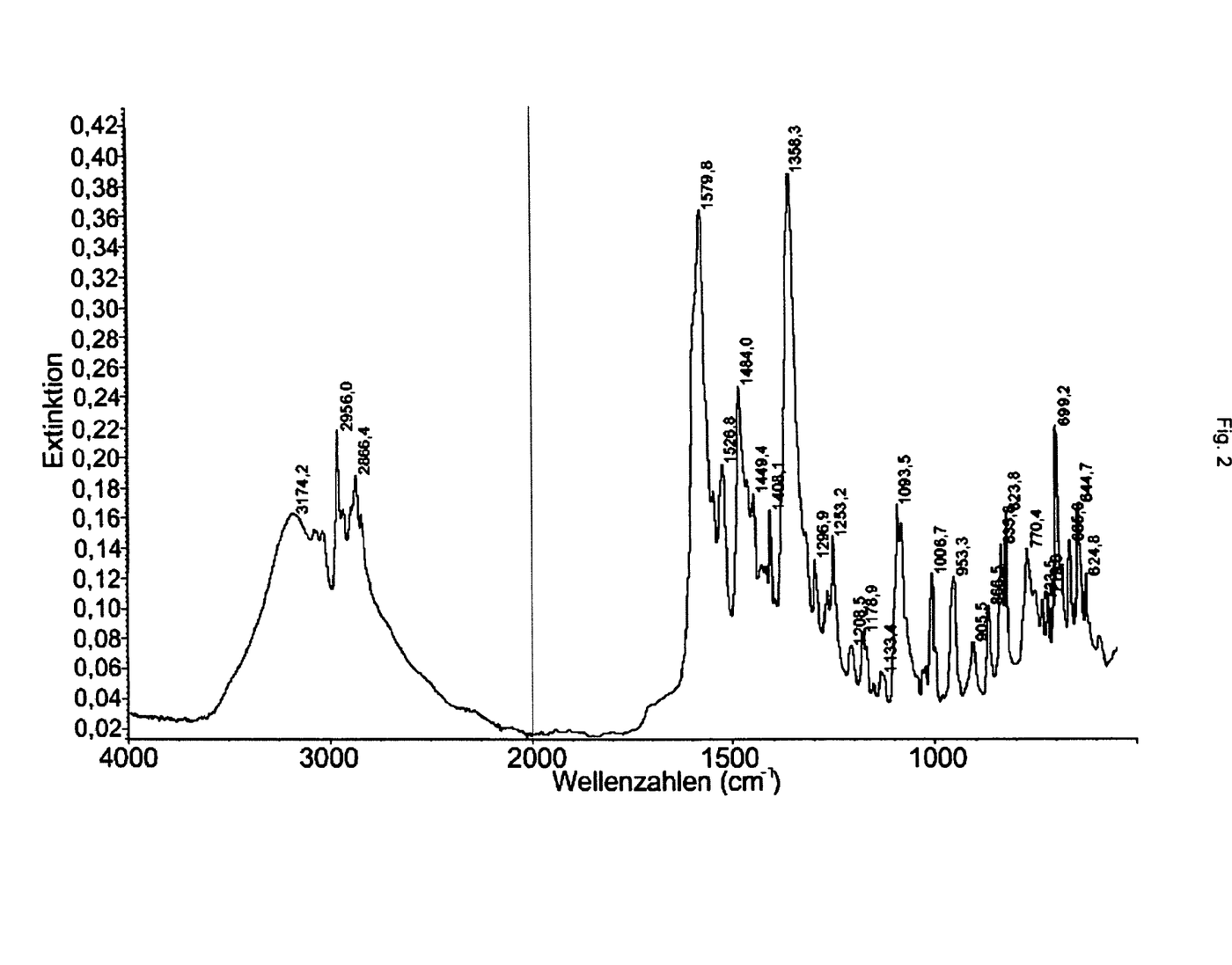
FIG. 2 the IR-spectrum of the choline salt prepared in example 1B.

X-ray diffraction diagram and IR-spectrum of the choline salt are shown in FIGS. 1B and 2, respectively.

Example 2

Preparation of 6-(4-chlorophenyl)-2,2-dimethyl-7-phenyl-2,3-dihydro-1H-pyrrolizin-5-ylacetic acid tromethamine salt Licofelone (2.25 kg) was slurried in ethanol (59.2 l). The slurry was heated to 47° C. until dissolution. Tromethamol (0.79 kg) was introduced maintaining the temperature at 47° C. and the resulting slurry was stirred at 47° C. for 1 h. Diisopropylether (14.8 l) was added in 15 min maintaining the temperature at 47° C. The suspension was cooled in 3 h to 27° C., stirred at this temperature for about 1 h, further cooled to −13° C. in 1 h and stirred at this temperature for 2 h. The product was centrifuged and the cake was washed with cold diisopropylether (7.1 l). The wet cake was dried at approx. 80° C. for 15 h.

Yield: 2.73 kg (=92%), chemical purity (HPLC): >99.9% (water content: 0.1%)

Figure 3:
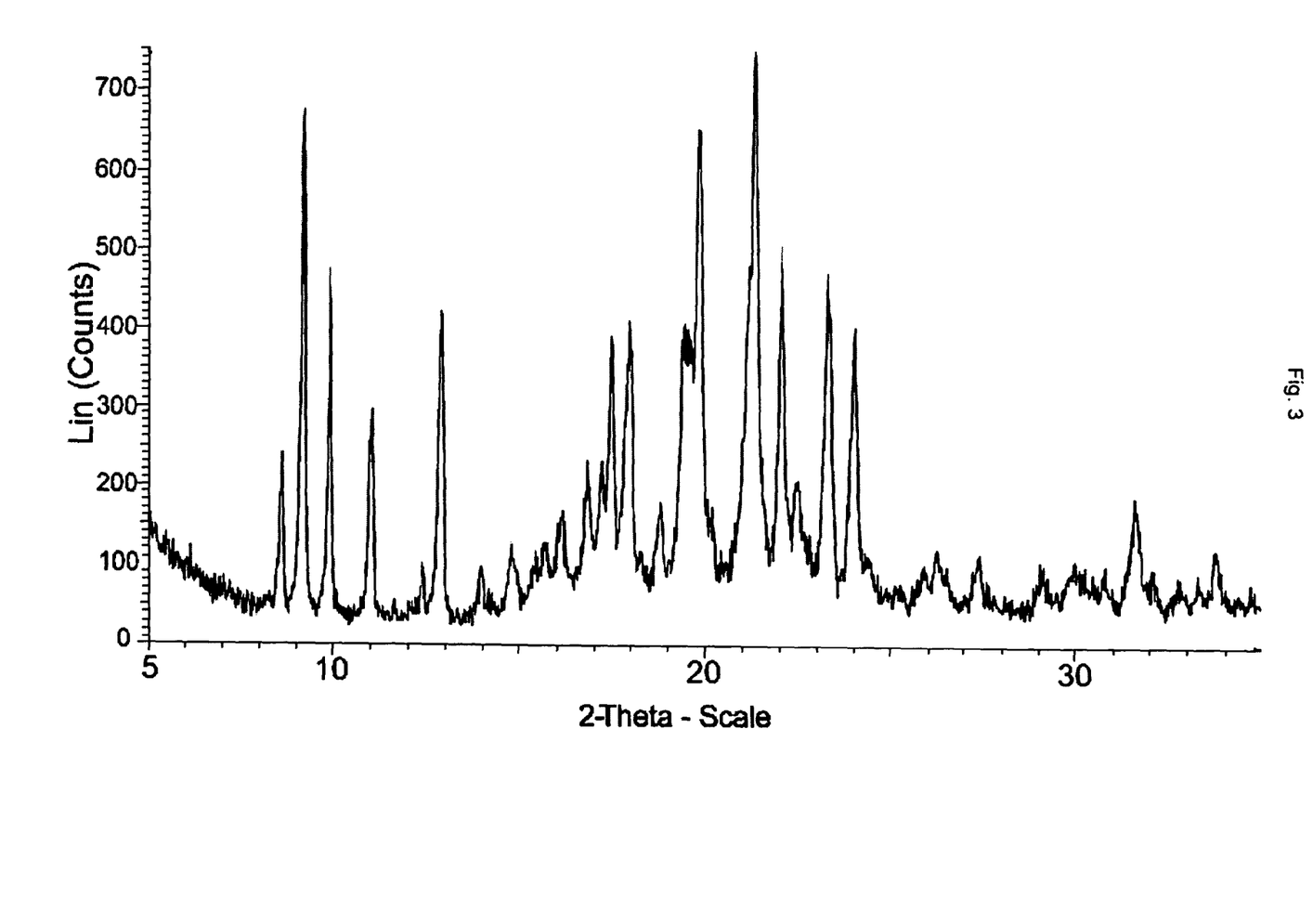
FIG. 3 the X-ray powder diffractogram of the tromethamine salt prepared in example 2.
Figure 4:
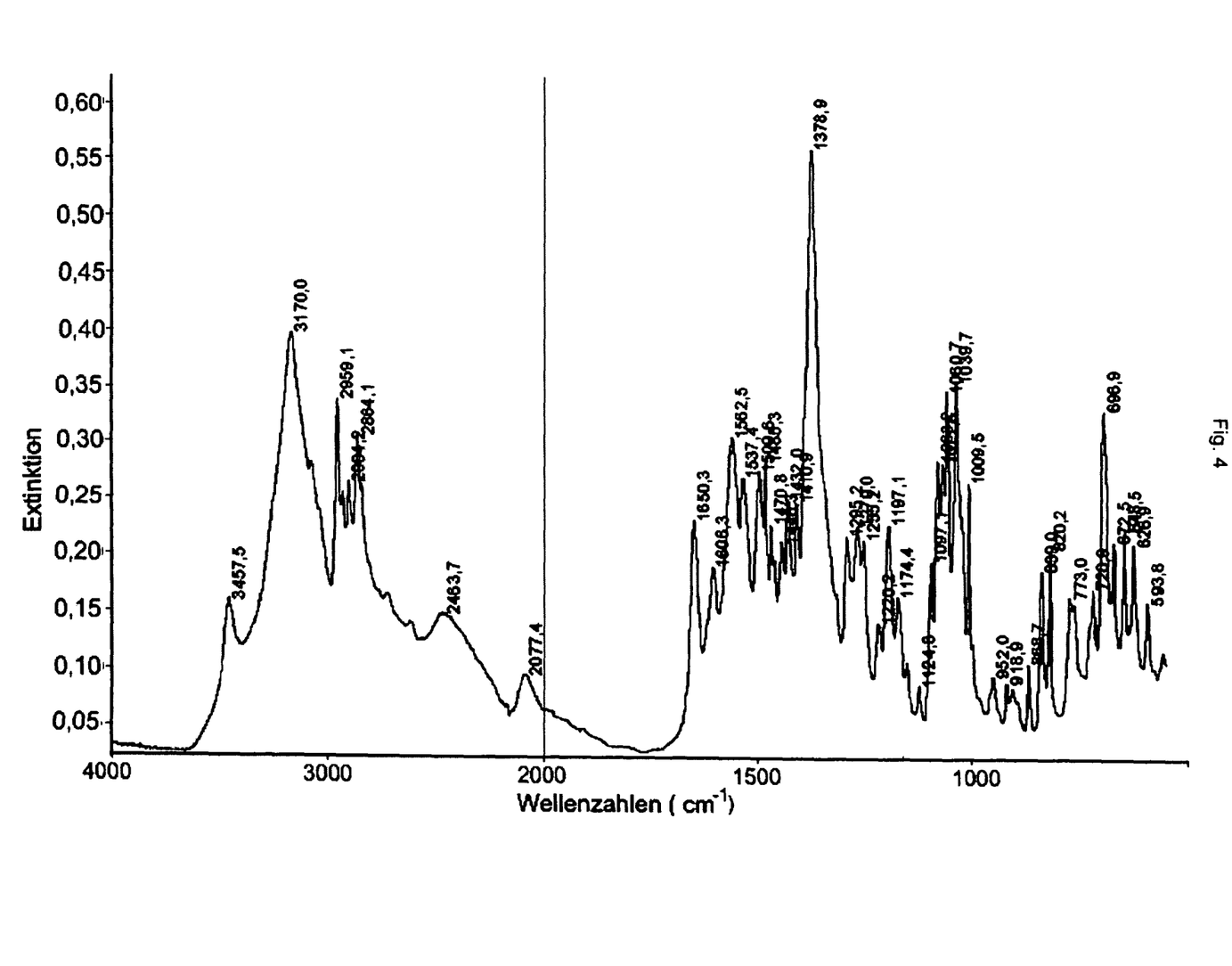
FIG. 4 the IR-spectrum of the tromethamine salt prepared in example 2.

X-ray diffraction diagram and IR-spectrum of the tromethamine salt are shown in FIGS. 3 and 4, respectively.

Example 3

Pharmaceutical composition comprising 6-(4-chlorophenyl)-2,2-dimethyl-7-phenyl-2,3-dihydro-1H-pyrrolizin-5-ylacetic acid choline salt Tablets containing the following ingredients were prepared in a conventional manner.
127.2 mg Licofelone-choline salt (corresponding to 100 mg Licofelone free acid)
20 mg Na-carboxymethylcellulose
90 mg microcrystalline cellulose
116 mg Sepistab
16 mg Kolidon
5 mg Talkum
3 mg Mg-stearat Tablets containing the following ingredients were prepared in a conventional manner.
63.6 mg Licofelone-choline salt (corresponding to 50 mg Licofelone free acid)
8 mg Kollidon VA 64
120 mg Pharmaburst
25 mg Kollidon CL
290 mg Mannitol
5 mg Mg-stearat

Example 4

Pharmaceutical composition comprising 6-(4-chlorophenyl)-2,2-dimethyl-7-phenyl-2,3-dihydro-1H-pyrrolizin-5-ylacetic acid tromethamine salt Tablets containing the following ingredients were prepared in a conventional manner.
131.9 mg Licofelone-tromethamine salt (corresponding to 100 mg Licofelone free acid)
20 mg Na-carboxymethylcellulose
88 mg microcrystalline cellulose
100 mg Sepistab
16 mg Kolidon
5 mg Talkum
3 mg Mg-stearat Tablets containing the following ingredients were prepared in a conventional manner.
65.95 mg ML3000-choline salt (corresponding to 50 mg Licofelone free acid)
8 mg Kollidon VA 64
120 mg Pharmaburst
25 mg Kollidon CL
290 mg Mannitol
5 mg Mg-stearat

Example 5

Solubility of 6-(4-chlorophenyl)-2,2-dimethyl-7-phenyl-2,3-dihydro-1H-pyrrolizin-5-ylacetic acid choline salt and 6-(4-chlorophenyl)-2,2-dimethyl-7-phenyl-2,3-dihydro-1H-pyrrolizin-5-ylacetic acid tromethamine salt as compared to 6-(4-chlorophenyl)-2,2-dimethyl-7-phenyl-2,3-dihydro-1H-pyrrolizin-5-ylacetic acid 5.1. Solubility in 2-pyrrolidone Approx. 500 mg Licofelone (free acid) or the corresponding salt (examples 1A and 2) were suspended in 1 ml 2-pyrrolidone and mixed for 30 min. The temperature was maintained at 25° C. After centrifugation the concentration of Licofelone in the supernatant was determined by HPLC with UV detection. The results are summarized in table 1.

TABLE 1

| compound | solubility [mg/mL] |
|---|---|
| Licofelone (free acid) | 47 |
| Licofelone tromethamine salt | 66 |
| Licofelone choline salt | 274 |

5.2. Solubility in Fasted State Simulated Intestinal Fluid (FaSSIF)

FaSSIF was prepared according to the literature (e.g. Marques M, Dissolution Technologies, May 2004). Blank FaSSIF was prepared by dissolving 1.74 g NaOH pellets, 19.77 g $Na_2HPO_4 \cdot H_2O$ and 30.93 g NaCl in 5 l water. The pH value was adjusted to 6.5 using 1 N NaOH. The ready-to-use FaSSIF was prepared by dissolving 3.3 g sodium taurocholate in 500 ml blank FaSSIF. Then, 11.8 ml of a solution of 100 mg/ml lecithin in dichloromethane was added and the thereafter, the solvent dichloromethane was removed under vacuum at 40° C. Thereafter the clear solution was transferred into a graduated 2 l flask and made up to volume with blank FaSSIF.

Solubility studies were performed with Licofelone (free acid), Licofelone tromethamol salt (example 2) and Licofelone choline salt (example 1A). The test articles were placed in a beaker, FaSSIF and a magnetic stirring bar were added and the mixture was stirred using a magnetic stirrer. After 15 min, samples were withdrawn, filtered and the clear filtrate was analyzed by HPLC to determine the concentration of Licofelone.

The dissolution test was performed in 100 ml FaSSIF and 30 ml FaSSIF. The lower volume was selected in order to simulate the physiological ratio between drug and intestinal fluid volume.

| compound | solubility in 100 ml FaSSIF | | solubility in 30 ml FaSSIF | |
|---|---|---|---|---|
| | weight* [mg] | conc. [mg/mL] | weight* [mg] | conc. [mg/mL] |
| Licofelone (free acid) | 51.4 | 0.007 | 50.8 | 0.007 |
| Licofelone tromethamine salt | 49.7 | 0.165 | 50.2 | 0.149 |
| Licofelone choline salt | 50.6 | 0.228 | 50.3 | 0.222 |

*related to Licofelone (free acid)

Example 6

Figure 5:
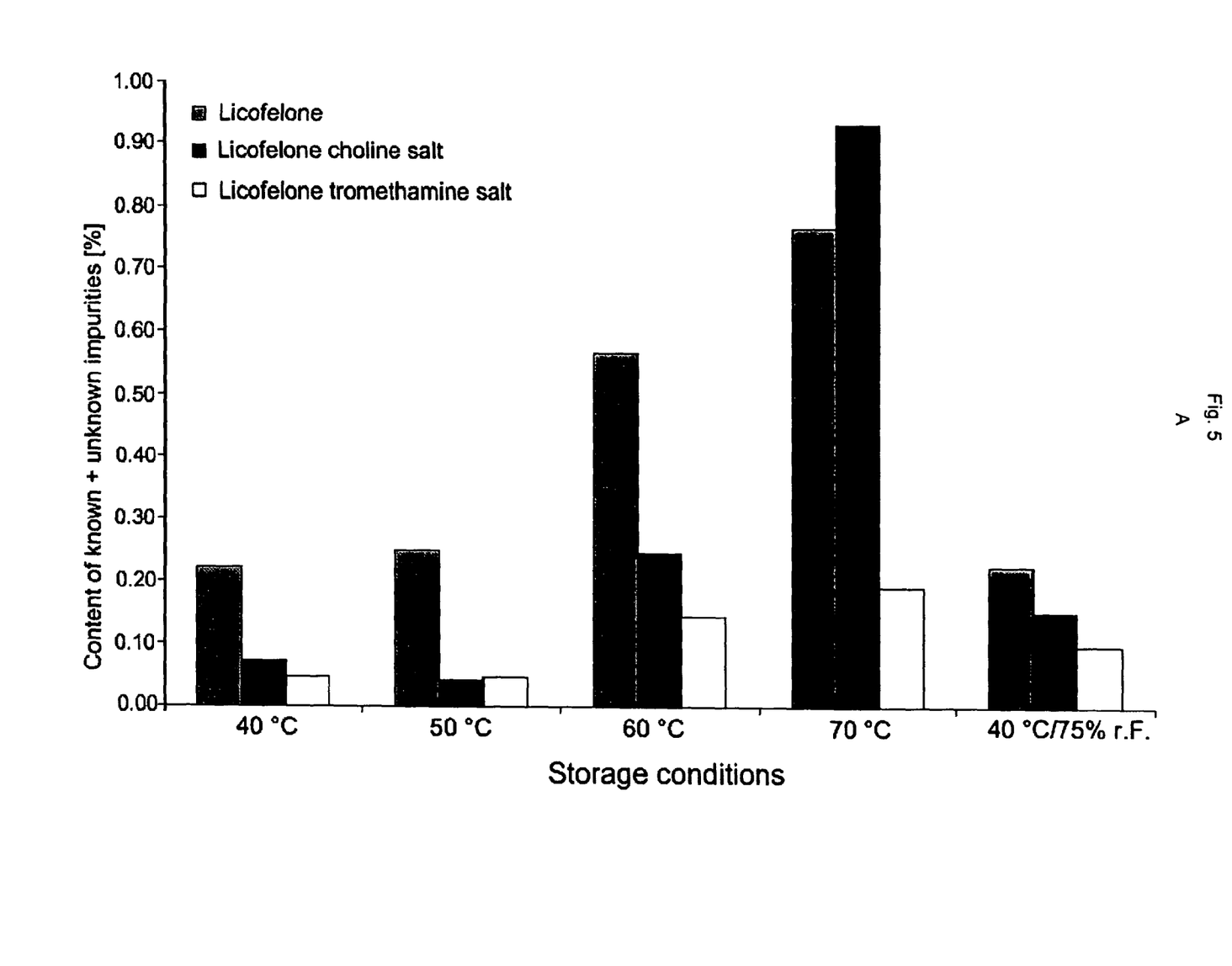
FIG. 5 the sum of known and unknown impurities in Licofelone, Licofelone choline salt (prepared in Example 1B) and Licofelone tromethamine salt (prepared in example 2) after storage at elevated temperatures for (A) 4 weeks and (B) 8 weeks.

Stability of 6-(4-chlorophenyl)-2,2-dimethyl-7-phenyl-2,3-dihydro-1H-pyrrolizin-5-ylacetic acid choline salt and 6-(4-chlorophenyl)-2,2-dimethyl-7-phenyl-2,3-dihydro-1H-pyrrolizin-5-ylacetic acid tromethamine salt as compared to 6-(4-chlorophenyl)-2,2-dimethyl-7-phenyl-2,3-dihydro-1H-pyrrolizin-5-ylacetic acid The raw materials (a) Licofelone, (b) Licofelone choline salt (example 1A) and (c) Licofelone tromethamine salt (example 2) were stored in open containers at 40, 50, 60 and 70° C. as well as at 40° C. with 75% relative humidity. Samples were analyzed after storage periods of 4 and 8 weeks. A validated method was applied for quantification of the five known impurities as well as of unknown impurities. The results are shown in FIGS. 5A and 5A.

The invention claimed is:

1. A 6-(4-Chlorophenyl)-2,2-dimethyl-7-phenyl-2,3-dihydro-1H-pyrrolizin-5-ylacetic acid choline salt of the formula I 2. A pharmaceutical composition comprising the salt of claim 1, and one or more pharmaceutically acceptable excipients.

3. A method for the treatment of a rheumatoid disease which comprises administering to a subject in need of such treatment a therapeutically effective amount of the salt of claim 1.

* * * * *

UNITED STATES PATENT AND TRADEMARK OFFICE
CERTIFICATE OF CORRECTION

PATENT NO. : 8,519,155 B2  Page 1 of 1
APPLICATION NO. : 13/126216
DATED : August 27, 2013
INVENTOR(S) : Albrecht et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 15 days.

Signed and Sealed this

Fifteenth Day of September, 2015

Michelle K. Lee
*Director of the United States Patent and Trademark Office*